United States Patent [19]
Fobare et al.

[11] Patent Number: 5,164,505
[45] Date of Patent: Nov. 17, 1992

[54] N-PHENYL-N'-ALKYL-N'-PYRIDYLMETHYL-BIS-DIAMINO-5-METHYLENE-1,3-DIOXANE-4,6-DIONES

[75] Inventors: William F. Fobare, Hamilton, N.J.; Donald P. Strike, St. Davids, Pa.; Patrick M. Andrae, Plainsboro, N.J.

[73] Assignee: American Home Products Corporation, New York, N.Y.

[21] Appl. No.: 879,494

[22] Filed: May 7, 1992

[51] Int. Cl.$^5$ ............................................. C07D 405/12
[52] U.S. Cl. ..................................................... 546/268
[58] Field of Search ......................................... 546/268

[56] References Cited

U.S. PATENT DOCUMENTS

| | | | |
|---|---|---|---|
| 3,907,798 | 9/1975 | Lesher | 549/274 X |
| 4,008,067 | 2/1977 | Hirono et al. | 549/274 X |
| 4,118,557 | 10/1978 | Lesher | 546/268 |
| 4,387,105 | 6/1983 | De Vries et al. | 424/322 |
| 4,387,106 | 6/1983 | De Vries et al. | 424/322 |

FOREIGN PATENT DOCUMENTS 1147759  4/1969  United Kingdom.

OTHER PUBLICATIONS

J. Med. Chem. 29, 1131 (1986), De Vries et al.
Stephen, Monat. Fur Chemie, 97, 45 (1966).
Derwent Abstract 40365K (1983).
Augustin et al., Z. Chem. 30, 169 (1990).
Wiss. Z. Univ. Hall XXXVIII 1989 M, H.3, 527-36, Augustin et al.
Synthesis, pp. 317-320 (1989), Ye et al.
Chem. Abstract 71(23) 112900 (1969), Boehme et al.

Primary Examiner—Marianne M. Cintins
Assistant Examiner—Michael B. Hydorn
Attorney, Agent, or Firm—Richard K. Jackson

[57] ABSTRACT

A compound of the formula:

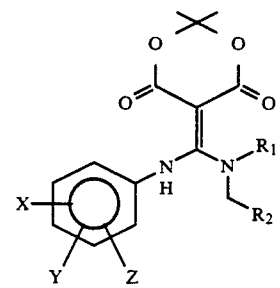

wherein: X, Y and Z, independently, are hydrogen, halogen, hydroxy, nitro, cyano, carboxyl, trifluoromethyl, phenyl, amino, mono and di-alkylamino, $C_1$-$C_{12}$ alkyl or $C_1$-$C_{12}$ alkoxy; $R_1$ is hydrogen, $C_1$-$C_{18}$ saturated or unsaturated alkyl, cycloalkyl, phenyl, benzyl or substituted benzyl where the substituents are $C_1$-$C_{12}$ alkyl, or $C_1$-$C_{12}$ alkoxy; and $R_2$ is represented by 2.

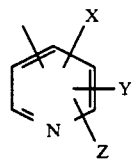

in which X, Y, and Z are defined above; or a pharmaceutically acceptable salt thereof.

8 Claims, No Drawings

N-PHENYL-N'-ALKYL-N'-PYRIDYLMETHYL-BIS-DIAMINO-5-METHYLENE-1,3-DIOXANE-4,6-DIONES

BACKGROUND OF THE INVENTION

This invention relates to chemical compounds which inhibit Acyl-Coenzyme A: Cholesterol-Acyl Transferase (ACAT). Compounds which possess that property are useful in reducing cholesterol absorption and in the treatment of atherosclerosis.

Atherosclerosis is the most common form of arteriosclerosis and is characterized by the build-up of phospholipids and esterified cholesterol in large and medium arteries causing them to be inelastic and thus weakened. These inelastic and occluded arteries are the most common cause of ischemic heart disease.

ACAT is an important enzyme for the intracellular esterification of cholesterol. Studies of this enzyme in cultured cells (M.S. Brown, *J. Biol. Chem.* 1980, 617, 458) has shown that increases in ACAT activity represent increases in the presence of cholesterol laden lipoproteins. Regulation of ACAT may be used to help prevent the absorption of cholesterol in the intestinal mucosa, and assist in the reversal of already present atherosclerotic lesions.

DESCRIPTION OF THE INVENTION

This invention provides a series of novel compounds of general formula 1 which inhibit Acyl-CoA: Cholesterol Acyltransferase (ACAT);

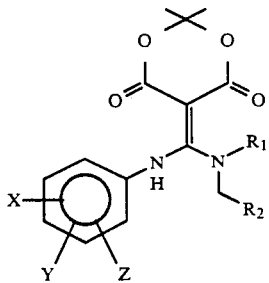

wherein:
X,Y and Z, independently, are hydrogen, halogen, hydroxy, nitro, cyano, carboxyl, trifluoromethyl, phenyl, amino, mono and di-alkylamino, in which each alkyl group contains 1-12 carbon atoms, $C_1$–$C_{12}$ alkyl or $C_1$–$C_{12}$ alkoxy;

$R_1$ is hydrogen, $C_1$–$C_{18}$ saturated or unsaturated alkyl, cycloalkyl, phenyl, benzyl or substituted benzyl where the substituents are $C_1$–$C_{12}$ alkyl, or $C_1$–$C_{12}$ alkoxy; and $R_2$ is represented by 2.

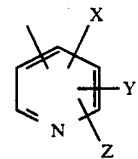

in which X, Y, and Z are defined above;
or a pharmaceutically acceptable salt thereof.

The halogen substituted referred to above may be chlorine, bromine, fluorine or iodine. The pharmaceutically acceptable salts are derived from known inorganic and organic acids such as hydrochloric, hydrobromic, sulfuric, nitric, phosphoric. methanesulfonic, ethanesulfonic, hydroxyethanesulfonic, toluene sulfonic, naphthalenesulfonic, formic, acetic, propionic, oxalic, succinic, glycollic, lactic, malic, tartaric, citric, ascorbic, maleic, hydroxymaleic, pyruvic, phenylacetic, benzoic, paraamino benzoic, para-hydroxybenzoic, salicylic, sulfanilic acids, and the like.

Of these compounds, those preferred on the basis of their in vitro and in vivo potency are those of formula 3:

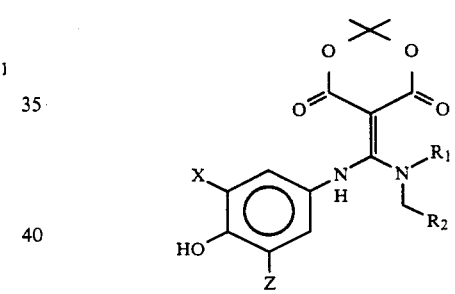

in which
X and Z are, independently, alpha branched alkyl of 1 to 6 carbon atoms;
$R_1$ is alkyl of 1 to 18 carbon atoms; and
$R_2$ is 2-, 3- or 4-pyridinyl;
or a pharmaceutically acceptable salt thereof.

The compounds of this invention may be prepared by the following reaction scheme, starting with the commercially available 2,2-dimethyl-1,3-dioxane-4,6-dione (Meldrum's):

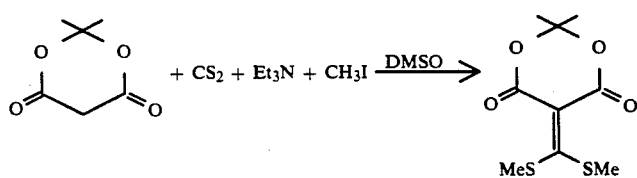

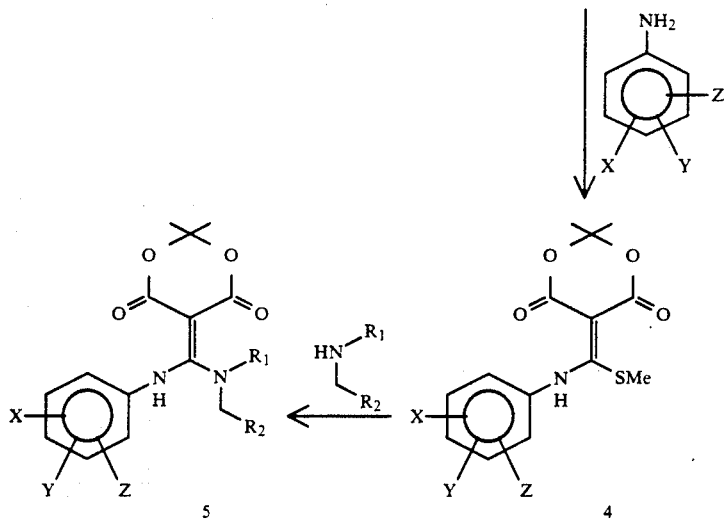

The following examples show the preparation of representative compounds of the invention.

METHOD A

EXAMPLE 1

5-[(3,5-Di-tert-butyl-4-hydroxy-phenylamino)-(hexyl-(pyridin-4-ylmethyl)-amino)-methylene]-2,2-dimethyl-1,3-dioxane-4,6-dione

Procedure 1

To a solution of 6.4 g (25.8 mmol) of 5-[bis(methylthio)methylene]-2,2-dimethyl-1,3-dioxane-4,6-dione and 4.84 g (56.0 mmol) of sodium bicarbonate in 10 mL of degassed DMSO was added 10.0 g (36.0 mmol) of 3,5-di-t-butyl-4-hydroxyaniline hydrochloride in 30 mL of degassed DMSO over a 5 hour period at room temperature. Stirring was continued for an additional 19 hours. The reaction mixture was poured into cold $H_2O$ and the product filtered. The solid was dried and dissolved in ethyl acetate and filtered again. The solvent was removed at reduced pressure and the residue submitted to a column chromatography on silica gel (3:1 to 2:1 hexane-ethyl acetate) to yield 9.8 g (90%) of a solid that was used without further purification.

Procedure 2

To a solution of 9.9 gm (91.85 mmol) of 2-aminomethylpyridine in 40 mL of methanol was added HCl saturated methanol to pH=7. Then 4.8 g (39.9 mmol) of hexaldehyde was added followed by 1.65 g (26.3 mmol) of sodium cyanoborohydride at room temperature. After stirring for 72 hours the mixture was acidified to pH=2 with concentrated HCl and the solvent was removed at reduced pressure. The residue was combined with 20 mL of $H_2O$ and extracted 3 times with 75 mL of diethyl ether. The aqueous layer was made basic (pH=14) with solid NaOH and extracted 3 times with 80 mL of ethyl acetate. The combined ethyl acetate layers were dried ($Na_2SO_4$) and the solvent removed at reduced pressure. Column chromatography of the residue on 300 g of silica gel (4% $MeOH-CHCl_3$) yielded 3.5 g (46%) of the amine which was used without further purification or characterization.

Procedure 3

To a solution of 0.97 g (2.3 mmol) of the material from Method A, procedure 1 in 20 mL of $CH_3CN$ was added 0.46 g (2.4 mmol) of the amine from Method A, procedure 2, 0.32 g (2.3 mmol) of $Et_3N$ and 0.41 g (1.38 mmol) of $HgSO_4$. The reaction mixture was allowed to reflux for 3.5 hours. The mixture was cooled to room temperature, filtered through celite and the solvents removed at reduced pressure. Column chromatography (1% ethanol-ethyl acetate to 3% ethanol-ethyl acetate) on 150 g of silica gel yielded 0.97 g of the title compound as a solid (mp 137°-140° C.) after recrystallization (isopropyl ether-ethyl acetate-hexanes). IR (KBr) 3260, 1952, 1868, 1625, 1432, 1386, 1362, 1242, 1199, 1161, 1114, 1086, 924, 783 and 733 $cm^{-1}$. $^1HNMR$ (400 MHz, $CDCl_3$): δ 9.61 (br s, 1H), 8.53 (d, 2H, J=4.9 Hz), 7.32 (br s, 2H) 6.79 (s, 2H), 5.29 (s, 1H), 4.28 (br s, 2H), 3.23 (br s, 2H), 1.65–1.57 (m, 8H), 1.38 (s, 18H), 1.20 (s, 6H), 0.83 (t, 3H, J=6.57 Hz).

Elemental analysis for $C_{33}H_{47}N_3O_5$: Calc'd: C, 70.06; H, 8.37; N, 7.43. Found: C, 70.01; H, 8.39; N, 7.08.

METHOD B

EXAMPLE 2

5-[[(2,4-Dimethoxyphenylamino)-[hexyl-(pyridin-4-ylmethyl)-amino]-methylene]-2,2-dimethyl-[1,3]-dioxane-4,6-dione

Procedure 1

To a solution containing 2.0 g (8.05 mmol) of 5-[bis(-methylthio)methylene]-2,2-dimethyl-1,3-dioxane-4,6-dione in 40 mL of t-butanol, was added 1.23 g (8.05 mmol) of 2,4-dimethoxyaniline. The reaction mixture was cooled to room temperature and diluted with hexanes. The solid was filtered and used without further purification. Isolated: 2.3 g, 81% yield.

Procedure 2

To a solution of 0.93 g (2.61 mmol) of the product from Method B, procedure 1, in 15 mL of $CH_3CN$ was added 0.33 g (2.7 mmol) of the amine from Method A, procedure 2, 0.46 g (1.37 mmol) of $HgSO_4$ and 0.36 mL (2.6 mmol) of $Et_3N$. The reaction mixture was allowed to reflux for 17 hours. The mixture was cooled then diluted with ethyl acetate and filtered through celite. The solvents were removed at reduced pressure. The residue was chromatographed on silica gel (3% MeOH-CHCl$_3$). The oil obtained was crystallized (isopropylether-ethyl acetate-hexanes) to yield 1.01 g (78%) of the title compound as a solid (mp 148°–150° C.). IR (KBr): 3440, 3220, 2992 2932, 2858, 1689, 1621, 1509, 1461, 1434, 1413, 1382, 1347, 1309, 1260, 1204, 1157, 1132, 1080, 1028, 926, 829, 783 and 724 cm$^{-1}$. $^1$H NMR (400 MHz, CDCl$_3$): δ 9.01 (br s, 1H), 8.56 (d, 2H, J=5.92 Hz), 7.36 (d, 2H, J=5.07 Hz), 7.04 (d, 1H, J=8.45 Hz), 6.46 (m, 2H), 4.35 (br s, 2H), 3.82 (s, 3H), 3.73 (s, 3H), 3.23 (t, 2H, J=6.88 Hz), 1.64–1.51 (m, 8H), 1.20 (br s, 6H), 0.85 (t, 3H, J=6.78 Hz).

Elemental analysis for C$_{27}$H$_{35}$N$_3$O$_6$: Calc'd: C, 65.17; H, 7.09; N, 8.44. Found: C, 65.18; H, 7.25; N, 8.29.

EXAMPLE 3

5-[(3,5-Di-tert-butyl-4-hydroxy-phenylamino)-(hexyl-(pyridin-2-ylmethyl)-amino]-methylene]-2,2-dimethyl-[1,3]-dioxane-4,6-dione This compound was synthesized using the procedure in Method A except 2-aminomethylpyridine was used instead of 4-aminomethylpyridine to yield (91%) a solid (mp 169°–170° C.).

Elemental analysis for C$_{33}$H$_{47}$N$_3$O$_5$: Calc'd: C, 70.06; H, 8.34; N, 7.43. Found: C, 70.05; H, 8.47; N, 6.98.

EXAMPLE 4

5-[(2,4-Dimethoxyphenylamino)-[hexyl-(pyridin-2-ylmethyl)-amino]-methylene]-2,2-dimethyl-[1,3]-dioxane-4,6-dione This compound was synthesized using the procedure in Method B except 2-aminomethyl-pyridine was used instead of 4-aminomethylpyridine to yield(82%) a solid (mp 104°–105° C.).

Elemental analysis for C$_{27}$H$_{35}$N$_3$O$_6$: Calc'd: C, 65.17; H, 7.09; N, 8.44. Found: C, 64.92; H, 7.08; N, 8.22.

EXAMPLE 5

5-[(2,4-Dimethoxy-phenylamino)-[hexyl-(pyridin-3-ylmethyl)-amino]-methylene]-2,2-dimethyl-[1,3]-dioxane-4,6-dione This compound was synthesized using the procedure in Method B except 3-aminomethyl-pyridine was used instead of 4-aminomethylpyridine to yield (95%) a solid (mp 154°–155° C.).

Elemental analysis for C$_{27}$H$_{35}$N$_5$O$_6$: Calc'd: C, 65.17; H, 7.09; N, 8.44. Found: C, 64.87; H, 7.12; N, 8.30.

EXAMPLE 6

5-[(3,5-Di-tert-butyl-4-hydroxy-phenylamino)-[hexyl-(pyridin-3-ylmethyl)-amino]-methylene]-2,2-dimethyl-1,3-dioxane-4,6-dione This compound was synthesized using the procedure in Method A except 3-aminomethylpyridine was used instead of 4-aminomethylpyridine to yield (78%) a solid (mp 134°–136° C.).

Elemental analysis for C$_{33}$H$_{47}$N$_3$O$_5$: Calc'd: C, 70.06; H, 8.37; N, 7.43. Found: C, 70.25; H, 8.57; N, 7.09.

The ability of the compounds of this invention to inhibit acyl-coenzyme A: cholesterol acyltransferase was established by initially showing that they inhibited intracellular cholesterol esterification by subjecting them to the standard experimental test procedure of Ross et al., J. Biol. Chem 259 815 (1984). The results of these studies are presented in Table 1:

TABLE 1

| Example | In Vitro % Inhib. (Concentration - μM) | IC$_{50}$ (μM) |
| --- | --- | --- |
| 1 | 94 (25) | 5.82 |
| 2 | 24 (25) | — |
| 3 | 92 (25) | 4.11 |
| 4 | 26 (25) | — |
| 5 | 18 (25) | — |
| 6 | 97 (25) | 3.9 |

Representative compounds were further tested in vivo to establish the percent inhibition of cholesterol absorption. In this study, normal rats were dosed (oral gavage) with $^{14}$C-cholesterol. plus the test compound. Blood samples taken exactly six hours later were analyzed and the percent inhibition of cholesterol absorption was calculated as shown in Table 2

TABLE 2

| In Vivo Testing $^{14}$C-cholesterol Absorption in Normal Rats | | |
| --- | --- | --- |
| Example | Dose mg/kg | % Inhibition of Absorption |
| 3 | 10 | 65% |
| 6 | 3 | 48% |

From these data, the ability of the compounds to inhibit ACAT is clearly established. Hence, the compounds of this invention are useful in the treatment of those disease states which are amenable to treatment by reduction of the rate of cholesterol esterification, the rate of accumulation and deposits of cholesteryl esters on arterial walls and the rate of formation of atheromatous lesions. As such, the antiatherosclerotic agents of this invention may be administered to a mammal in need of intracellular cholesteryl ester concentration reduction orally or parenterally in an amount sufficient to inhibit ACAT catalysis of cholesterol esterification.

The compounds of this invention may be administered by themselves or in combination with pharmaceutically acceptable liquid or solid carriers. Oral administration in conventional formulations as tablets, capsules, powders, or suspensions is preferred.

A solid carrier can include one or more substances which may also act as flavoring agents, lubricants, solubilisers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both of pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g., glycols) and their derivatives, and oils (e.g. fractionated coconut oil and arachis oil). For parenteral administration, the carrier can also be an oil ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular intraperitoneal or subcutaneous injection. Sterile solutions can also be administered intravenously. When the compound is orally active, it can be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific hypercholesterolemic/atherosclerotic condition must be subjectively determined by the attending physician. The variables involved include the extent of the disease state, size, age and response pattern of the patient.

What is claimed is:

1. A compound of structural formula 1:

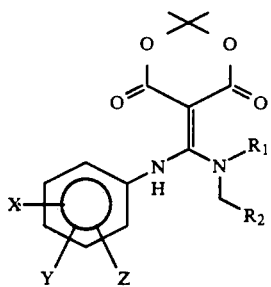

wherein:

X, Y and Z, independently, are hydrogen, halogen, hydroxy, nitro, cyano, carboxyl, trifluoromethyl, phenyl, amino, mono and di $C_{1-12}$ alkylamino, alkylamino, $C_1$–$C_{12}$ alkyl or $C_1$–$C_{12}$ alkoxy;

$R_1$ is hydrogen, $C_1$–$C_{18}$ saturated or unsaturated alkyl, cycloalkyl, phenyl, benzyl or substituted benzyl where the substituents are $C_1$–$C_{12}$ alkyl, or $C_1$–$C_{12}$ alkoxy; and $R_2$ is represented by structural formula 2.

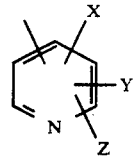

in which X, Y, and Z are defined above; or a pharmaceutically acceptable salt thereof.

2. A compound of claim 1 structural formula 3:

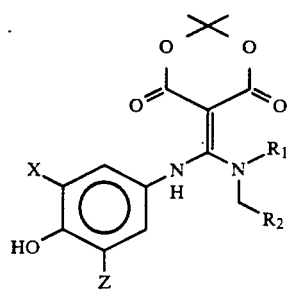

in which

X and Z are, independently, alpha branched alkyl of 1 to 6 carbon atoms;

$R_1$ is alkyl of 1 to 18 carbon atoms; and $R_2$ is 2-, 3- or 4- pyridinyl;

or a pharmaceutically acceptable salt thereof.

3. A compound of claim 1 which is 5-[(3,5-di-tert-butyl-4-hydroxyphenylamino)-(hexyl-(pyridin-4-ylmethyl)-amino)-methylene]-2,2-dimethyl-1,3-dioxane-4,6-dione, or a pharmaceutically acceptable salt thereof.

4. A compound of claim 1 which is 5-[[(2,4-dimethoxyphenylamino)-[hexyl-(pyridin-4-ylmethyl)-amino]-methylene]-2,2-dimethyl-[1,3]-dioxane-4,6-dione, or a pharmaceutically acceptable salt thereof.

5. A compound of claim 1 which is 5-[(3,5-di-tert-butyl-4-hydroxyphenylamino)-(hexyl-(pyridin-2-ylmethyl)-amino]-methylene]-2,2-dimethyl-[1,3]-dioxane-4,6-dione, or a pharmaceutically acceptable salt thereof.

6. A compound of claim 1 which is 5-[(2,4-dimethoxyphenylamino)-[hexyl-(pyridin-2-ylmethyl)-amino]-methylene]-2,2-dimethyl-[1,3]-dioxane-4,6-dione, or a pharmaceutically acceptable salt thereof.

7. A compound of claim 1 which is 5-[(2,4-dimethoxy-phenylamino)-[hexyl-(pyridin-3-ylmethyl)-amino]-methylene]-2,2-dimethyl-[1,3]-dioxane-4,6-dione, or a pharmaceutically acceptable salt thereof.

8. A compound of claim 1 which is 5-[(3,5-di-tert-butyl-4-hydroxyphenylamino)-[hexyl-(pyridin-3-ylmethyl)-amino]-methylene]-2,2-dimetyl-1,3-dioxane-4,6-dione, or a pharmaceutically acceptable salt thereof.

* * * * *